(12) United States Patent
Winslow et al.

(10) Patent No.: US 7,588,592 B2
(45) Date of Patent: *Sep. 15, 2009

(54) SYSTEM AND METHOD FOR IMMOBILIZING ADJACENT SPINOUS PROCESSES

(75) Inventors: Charles J. Winslow, Walnut Creek, CA (US); David Bohrer, Barrington, RI (US); Henry A. Klyce, Piedmont, CA (US)

(73) Assignee: Kyphon SARL, Neuchatel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/866,325

(22) Filed: Oct. 2, 2007

(65) Prior Publication Data

US 2008/0021472 A1    Jan. 24, 2008

Related U.S. Application Data

(63) Continuation of application No. 10/774,664, filed on Feb. 9, 2004, now Pat. No. 7,335,203.

(60) Provisional application No. 60/446,868, filed on Feb. 12, 2003.

(51) Int. Cl.
*A61B 17/70* (2006.01)

(52) U.S. Cl. .................. 606/249; 606/281; 606/71

(58) Field of Classification Search .................. 606/61, 606/69–71, 60, 246, 248–249, 257, 279, 606/280, 286, 292–293, 296, 900–902, 63
See application file for complete search history.

(56) References Cited

U.S. PATENT DOCUMENTS

| | | | |
|---|---|---|---|
| 2,677,369 A | | 5/1954 | Knowles |
| 3,426,364 A | * | 2/1969 | Lumb ...................... 623/17.15 |
| 3,648,691 A | * | 3/1972 | Lumb et al. .................. 606/279 |
| 4,011,602 A | | 3/1977 | Rybicki et al. |
| 4,257,409 A | | 3/1981 | Bacal et al. |
| 4,448,191 A | * | 5/1984 | Rodnyansky et al. ......... 606/61 |
| 4,554,914 A | * | 11/1985 | Kapp et al. .................... 606/61 |

(Continued)

FOREIGN PATENT DOCUMENTS

DE          2821678 A1    11/1979

(Continued)

OTHER PUBLICATIONS

Benzel et al., "Posterior Cervical Interspinous Compression Wiring and Fusion for Mid to Low Cervical Spinal Injuries," J. Neurosurg., Jun. 1989, ppp. 893-899, vol. 70.

(Continued)

*Primary Examiner*—Thomas C Barrett
*Assistant Examiner*—James L Swiger
(74) *Attorney, Agent, or Firm*—Coats and Bennett, P.L.L.C.

(57) ABSTRACT

A system and method for immobilizing adjacent spinous processes in accordance with the present invention can supplement primary fusion devices and methods by immobilizing spinous processes while bone from adjacent vertebral bodies grows together. The system requires less extensive surgical procedures than other common supplemental devices, and preferably does not require bone or ligament removal. One such system comprises three spacers positioned between spinous processes and adjustably connected with a plate positioned on either side of the spinous processes. Each plate includes grips, with each grip positioned adjacent to the spinous process, forming a clamp with a grip connected with the opposing plate.

20 Claims, 5 Drawing Sheets

U.S. PATENT DOCUMENTS

| | | | |
|---|---|---|---|
| 4,573,454 A | 3/1986 | Hoffman | |
| 4,604,995 A | 8/1986 | Stephens et al. | |
| 4,657,550 A * | 4/1987 | Daher | 623/17.11 |
| 4,686,970 A | 8/1987 | Dove et al. | |
| 4,827,918 A | 5/1989 | Olerud | |
| 4,836,196 A * | 6/1989 | Park et al. | 606/246 |
| 5,011,484 A | 4/1991 | Breard | |
| 5,047,055 A | 9/1991 | Bao et al. | |
| 5,092,866 A | 3/1992 | Breard et al. | |
| 5,201,734 A | 4/1993 | Cozad et al. | |
| 5,306,275 A | 4/1994 | Bryan | |
| 5,360,430 A | 11/1994 | Lin | |
| 5,366,455 A | 11/1994 | Dove | |
| 5,395,371 A * | 3/1995 | Miller et al. | 606/61 |
| 5,415,661 A | 5/1995 | Holmes | |
| 5,437,672 A | 8/1995 | Alleyne | |
| 5,454,812 A | 10/1995 | Lin | |
| 5,496,318 A | 3/1996 | Howland et al. | |
| 5,609,634 A | 3/1997 | Voydeville | |
| 5,628,756 A | 5/1997 | Barker, Jr. et al. | |
| 5,645,599 A | 7/1997 | Samani | |
| 5,674,295 A | 10/1997 | Ray et al. | |
| 5,676,702 A | 10/1997 | Ratron | |
| 5,690,649 A | 11/1997 | Li | |
| 5,776,197 A * | 7/1998 | Rabbe et al. | 623/17.15 |
| 5,810,815 A | 9/1998 | Morales | |
| 5,836,948 A | 11/1998 | Zucherman et al. | |
| 5,860,977 A | 1/1999 | Zucherman et al. | |
| 5,976,186 A | 11/1999 | Bao et al. | |
| 6,022,376 A | 2/2000 | Assell et al. | |
| 6,048,342 A | 4/2000 | Zucherman et al. | |
| 6,068,630 A | 5/2000 | Zucherman et al. | |
| 6,132,464 A | 10/2000 | Martin | |
| 6,156,038 A * | 12/2000 | Zucherman et al. | 606/61 |
| 6,176,881 B1 * | 1/2001 | Schar et al. | 623/17.11 |
| 6,203,548 B1 * | 3/2001 | Helland | 606/105 |
| 6,293,949 B1 | 9/2001 | Justis et al. | |
| 6,352,537 B1 | 3/2002 | Strnad | |
| 6,364,883 B1 * | 4/2002 | Santilli | 606/69 |
| 6,402,750 B1 | 6/2002 | Atkinson et al. | |
| 6,440,169 B1 | 8/2002 | Elberg et al. | |
| 6,451,019 B1 * | 9/2002 | Zucherman et al. | 606/61 |
| 6,494,893 B2 * | 12/2002 | Dubrul et al. | 606/185 |
| 6,582,433 B2 | 6/2003 | Yun | |
| 6,626,944 B1 | 9/2003 | Taylor | |
| 6,645,207 B2 | 11/2003 | Dixon et al. | |
| 6,648,891 B2 * | 11/2003 | Kim | 606/86 B |
| 6,695,842 B2 | 2/2004 | Zucherman et al. | |
| 6,709,435 B2 | 3/2004 | Lin | |
| 6,723,126 B1 | 4/2004 | Berry | |
| 6,733,534 B2 | 5/2004 | Sherman | |
| 6,761,720 B1 | 7/2004 | Senegas | |
| 6,835,205 B2 | 12/2004 | Atkinson et al. | |
| 6,946,000 B2 | 9/2005 | Senegas et al. | |
| 7,029,472 B1 * | 4/2006 | Fortin | 606/60 |
| 7,041,136 B2 | 5/2006 | Goble et al. | |
| 7,048,736 B2 | 5/2006 | Robinson et al. | |
| 7,087,083 B2 | 8/2006 | Pasquet et al. | |
| 7,163,558 B2 | 1/2007 | Senegas et al. | |
| 7,201,751 B2 | 4/2007 | Zucherman et al. | |
| 7,238,204 B2 | 7/2007 | Le Couedic et al. | |
| 7,306,628 B2 | 12/2007 | Zucherman et al. | |
| 7,442,208 B2 | 10/2008 | Mathieu et al. | |
| 7,445,637 B2 | 11/2008 | Taylor | |
| 2002/0143331 A1 * | 10/2002 | Zucherman et al. | 606/61 |
| 2003/0153915 A1 | 8/2003 | Nekozuka et al. | |
| 2004/0097931 A1 | 5/2004 | Mitchell | |
| 2005/0010293 A1 | 1/2005 | Zucherman et al. | |
| 2005/0049708 A1 | 3/2005 | Atkinson et al. | |
| 2005/0165398 A1 | 7/2005 | Reiley | |
| 2005/0203512 A1 | 9/2005 | Hawkins et al. | |
| 2005/0203624 A1 | 9/2005 | Serhan et al. | |
| 2005/0228391 A1 | 10/2005 | Levy et al. | |
| 2005/0261768 A1 | 11/2005 | Trieu | |
| 2005/0288672 A1 | 12/2005 | Feree | |
| 2006/0004447 A1 | 1/2006 | Mastrorio et al. | |
| 2006/0015181 A1 | 1/2006 | Elberg | |
| 2006/0064165 A1 | 3/2006 | Zucherman et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0089654 A1 | 4/2006 | Lins et al. | |
| 2006/0089719 A1 | 4/2006 | Trieu | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0122620 A1 | 6/2006 | Kim | |
| 2006/0136060 A1 | 6/2006 | Taylor | |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0264938 A1 | 11/2006 | Zucherman et al. | |
| 2006/0271044 A1 | 11/2006 | Petrini et al. | |
| 2006/0293662 A1 | 12/2006 | Boyer, II et al. | |

FOREIGN PATENT DOCUMENTS

| | | |
|---|---|---|
| EP | 0322334 B1 | 2/1992 |
| EP | 1138268 A1 | 10/2001 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2816197 A1 | 5/2002 |
| JP | 02-224660 | 9/1990 |
| JP | 09-075381 | 3/1997 |
| SU | 988281 | 1/1983 |
| WO | WO 94/26192 | 11/1994 |
| WO | WO 94/26195 | 11/1994 |
| WO | WO 98/20939 | 5/1998 |
| WO | WO 2004/047691 A1 | 6/2004 |
| WO | WO 2005/009300 A1 | 2/2005 |
| WO | WO 2005/044118 A1 | 5/2005 |
| WO | WO 2005/110258 A1 | 11/2005 |
| WO | WO 2007/034516 A1 | 3/2007 |

OTHER PUBLICATIONS

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," Spine, 2005, pp. S73-S78, vol. 30, No. 16S.

Cousin Biotech, Dispositif Intervertébral Amortissant, Jun. 1998, pp. 1-4.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," Spine, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," Spine, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Orthopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," Spine, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," Spine, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," Spine, 2005, pp. 744-749, vol. 30, No. 7.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," Spine, Jul. 1992, pp. 834-837, vol. 17, No. 7.

\* cited by examiner

SYSTEM AND METHOD FOR IMMOBILIZING ADJACENT SPINOUS PROCESSES

PRIORITY CLAIM

This application is a continuation of U.S. patent application Ser. No. 10/774,664, filed on Feb. 9, 2004 (now U.S. Pat. No. 7,335,203), which claims the benefit of U.S. Provisional Patent Application No. 60/446,868, filed Feb. 12, 2003, the full disclosures of which are incorporated herein by reference.

CROSS-REFERENCES TO RELATED APPLICATIONS

The following U.S. patent applications are cross-referenced and incorporated herein by reference:

U.S. patent application Ser. No. 09/829,321, entitled "SPINE FIXATION DEVICE AND METHOD" by David Yun, filed Apr. 9, 2001;

U.S. Provisional Patent Application No. 60/421,921, entitled "INTERSPINOUS PROCESS APPARATUS AND METHOD WITH A SELECTABLY EXPANDABLE SPACER" by James F. Zucherman, Ken Y. Hsu, and Charles J. Winslow, filed Oct. 29, 2002;

U.S. patent application Ser. No. 09/579,039, entitled SUPPLEMENTAL SPINE FIXATION DEVICE AND METHOD by James F. Zucherman, Ken Y. Hsu, Charles J. Winslow and Henry A. Klyce, filed May 26, 2000;

U.S. patent application Ser. No. 09/842,819, entitled SUPPLEMENTAL SPINE FIXATION DEVICE AND METHOD by James F. Zucherman, Ken Y. Hsu, Charles J. Winslow and Henry A. Klyce, filed Apr. 26, 2001;

U.S. patent application Ser. No. 09/982,418, entitled SUPPLEMENTAL SPINE FIXATION DEVICE AND METHOD by James F. Zucherman, Ken Y. Hsu, Charles J. Winslow, Steve Mitchell, Scott Yerby and Henry A. Klyce, filed Oct. 18, 2001;

U.S. Provisional Patent Application No. 60/306,262, entitled SUPPLEMENTAL SPINE FIXATION DEVICE AND METHOD by James F. Zucherman, Ken Y. Hsu, Charles J. Winslow, Steve Mitchell, Scott Yerby and Henry A. Klyce, filed Jul. 18, 2001;

U.S. Provisional Patent Application No. 60/421,915, entitled INTERSPINOUS PROCESS IMPLANT WITH RADIOLUCENT SPACER AND LEAD-IN TISSUE EXPANDER by James F. Zucherman, Ken Y. Hsu, Charles J. Winslow, John Flynn and Steve Mitchell, filed Oct. 29, 2002; and U.S. patent application Ser. No. 10/230,505, entitled DEFLECTABLE SPACER FOR USE AS AN INTERSPINOUS PROCESS IMPLANT AND METHOD by James F. Zucherman, Ken Y. Hsu, Charles J. Winslow and John Flynn, filed Aug. 29, 2002.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

1. Technical Field

The present invention relates to methods and systems for immobilizing adjacent spinous processes which, byway of example only, supplement a primary spine fusion device, such as an interbody fusion device.

2. Background

A common procedure for handling pain associated with degenerative spinal disk disease uses devices for fusing together two or more adjacent vertebral bodies. The procedure is known by a number of terms, one of which is interbody fusion. Interbody fusion can be accomplished through the use of a number of methods and devices known in the art. These methods and devices include screw arrangements, solid bone implant methodologies, and fusion devices which include a cage or other mechanism packed with bone and/or bone growth inducing substances. One or more of the above are implanted between adjacent vertebral bodies in order to fuse the vertebral bodies together, thereby alleviating associated pain.

It can be advantageous to associate with such primary fusion devices and methods, supplemental devices which assist in the fusion process. These supplemental devices assist during the several month period when bone from the adjacent vertebral bodies is growing together through the primary fusion device in order to fuse the adjacent vertebral bodies. During this period it is advantageous to have the vertebral bodies held immobile with respect to each other so that sufficient bone growth can be established.

Such supplemental devices can include hook and rod arrangements, screw arrangements, and a number of other devices which include straps, wires, and bands, all of which are used to immobilize one portion of the spine relative to another. All of these devices generally require extensive surgical procedures in addition to the extensive procedure surrounding the primary fusion implant.

It is advantageous for a device and procedure for supplemental spine fixation to be as simple and easy to perform as possible, and optimally such a device and procedure leaves bone, ligament, and other tissue which comprise and surround the spine intact.

BRIEF DESCRIPTION OF THE DRAWINGS

Further details of embodiments of the present invention are explained with the help of the attached drawings in which.

DETAILED DESCRIPTION OF THE INVENTION

Figure 1:
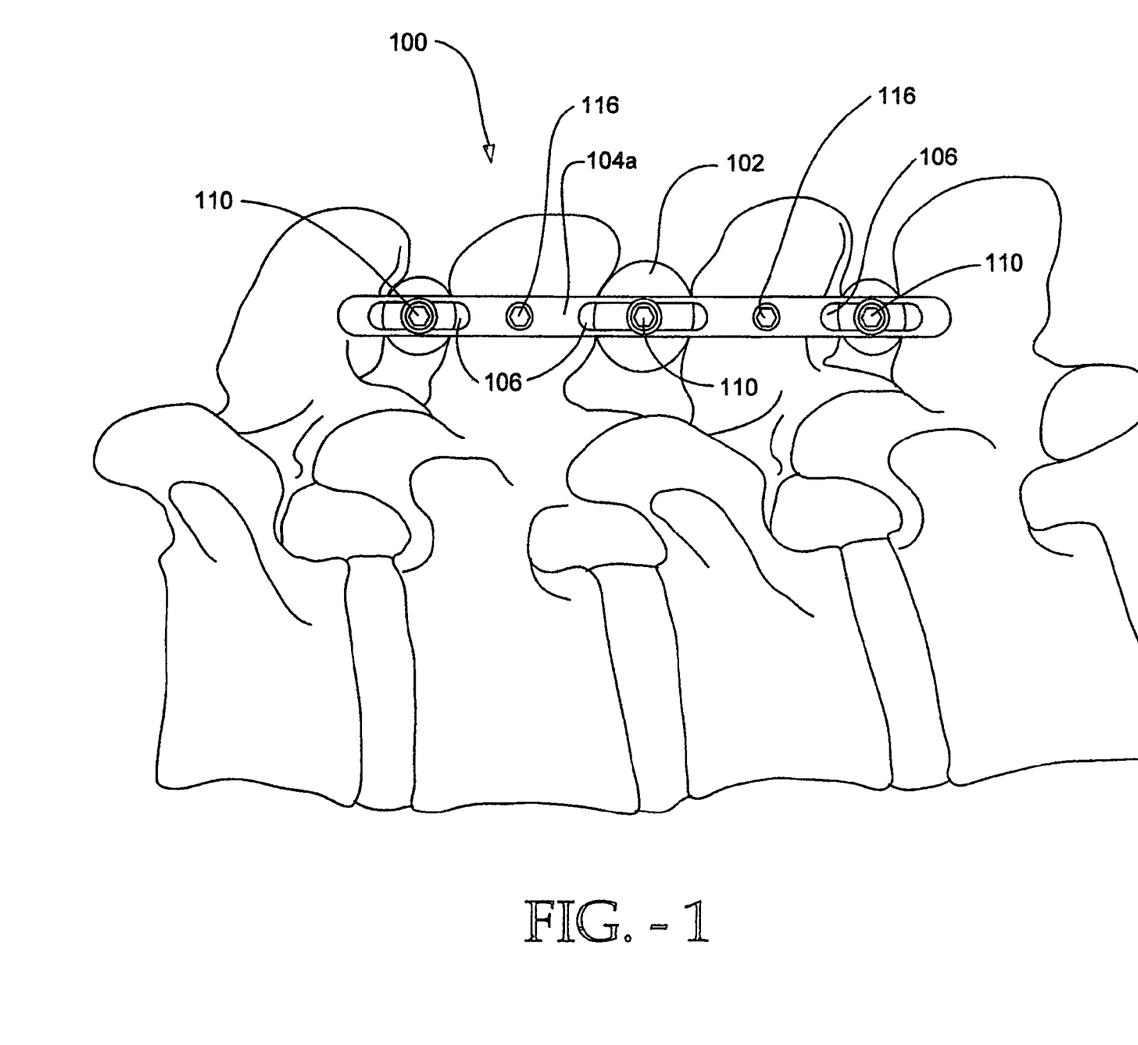
FIG. 1 is a side view of a system in accordance with one embodiment of the present invention positioned about adjacent spinous processes.
Figure 2A:
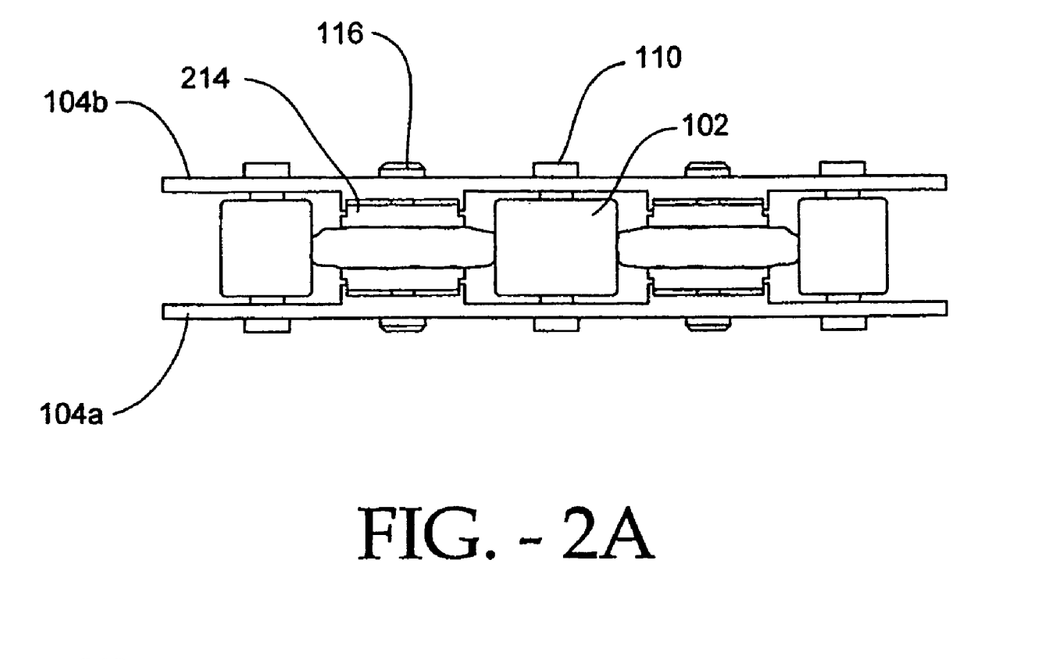
FIG. 2A is a top view of the system shown in FIG. 1.
Figure 2B:
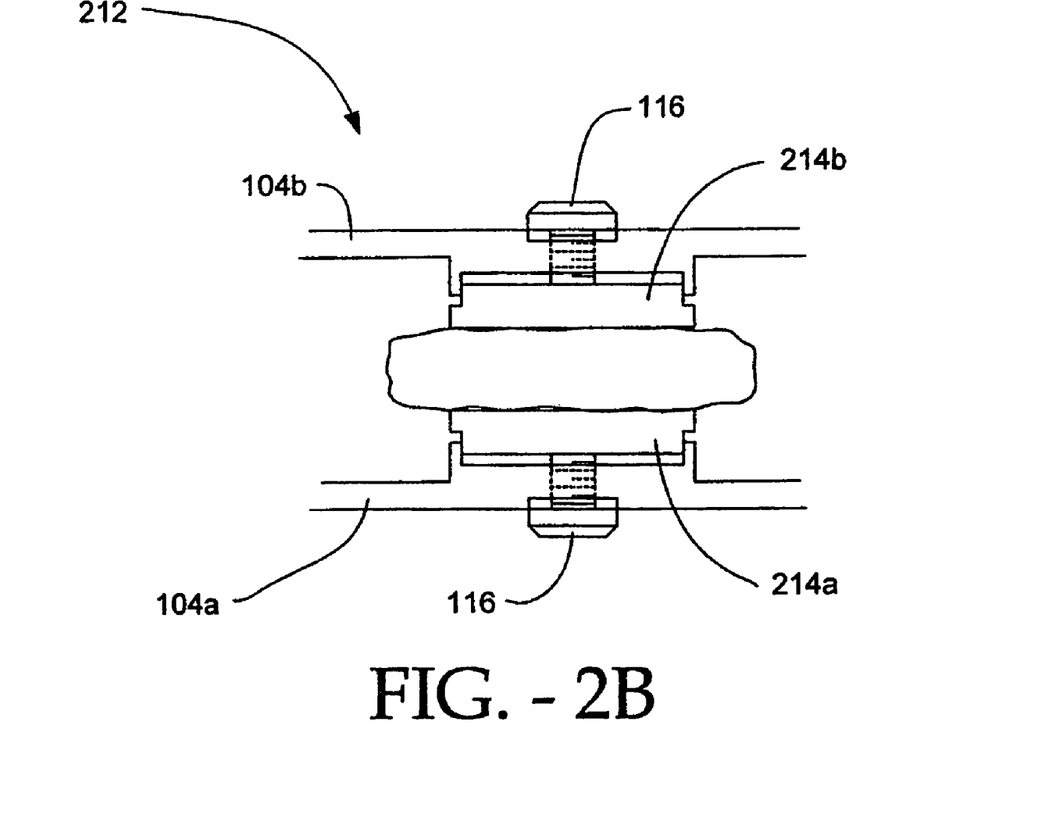
FIG. 2B is a close-up view of two grips positioned on opposite sides of a spinous process as shown in FIG. 2A.

FIGS. 1-2B illustrate a system for immobilizing adjacent spinous processes in accordance with one embodiment of the present invention. The system 100 comprises a scaffold formed by two plates 104a,b adjustably connected by pins 110 inserted through slots 106 in each plate. Each plate 104a,b is positioned generally along a plane parallel to a plane formed by the major axis of the spinous processes, with a first plate 104a positioned on one side of protruding adjacent spinous processes, and a second plate 104b positioned on an opposite side of the adjacent spinous processes, such that the spinous processes are sandwiched between the two plates. Each plate 104a,b includes two grips, each grip 214a,b comprising part of a clamp adapted for gripping the spinous processes to prevent shifting of the system 100 relative to the spine and to assist in immobilizing the adjacent spinous processes.

As shown in FIG. 2B, a clamp comprises a grip 214a from a first plate 104a and a grip 214b from a second plate 104b. The grip 214a from the first plate 104a is oriented such that the grip substantially opposes a face of a spinous process. The grip 214b from the second plate 104b is oriented such that the grip substantially opposes the opposite face of the spinous process. The grips 214a,b are spaced along the length of the plates 104a,b such that each pair of grips 214a,b is positioned about a spinous process. In other embodiments, and in the same way that spacers 102 are moveable in slots 106, the grips 214a,b can be moveably connected to grip slots in the plates 104a,b, thereby allowing each grip 214a,b to be moved laterally relative to every other grip 214a,b, thus allowing each grip 214a,b to be substantially centered with respect to an associated spinous process.

Each grip 214a,b is adjustably connected with an associated plate 104a,b by a threaded bolt 116 having preferably a hexagonal head for engaging the bolt 116. Twisting the threaded bolt 116 in a first direction drives the bolt 116, and consequently the grip 214a,b, toward the spinous process. Twisting the threaded bolt 116 in a direction opposite the first direction drives the grip 214a,b away from the spinous process. In other embodiments, the grip 214a,b can be connected to the plate 104a,b by a slotted screw. In still other embodiments, the grip 214a,b can be connected to the plate 104a,b by a socketed screw. One of ordinary skill in the art can appreciate the myriad of different fasteners that can be used to adjustably connect each grip 214a,b with an associated plate 104a,b.

The bolts 116 are provided through a threaded bore in the plates 104a,b. Turning the bolts 116 moves the bolts and the grips 214a,b secured thereto relative to the plates 104a,b. The ends of the bolts 116 can be either fixedly or rotatably secured to the grips 214a,b. The bolts 116 can be rotatably secured to the grips 214a,b as is know in the art. For example, the ends of the bolts can include a circumferential lip that is received in an undercut groove in a bore of the grips 214a,b. The lip is free to rotate in the groove of the bore. Where the bolts 116 are fixedly secured to the grips 214a,b, the grips 214a,b are preferably circular in cross-section (as the bolts 116 are tightened, the grips 214a,b rotate relative to the plates 104a,b and thus relative to the spinous processes). One of ordinary skill in the art can appreciate the different means for adjustably connecting the grip 214a,b with the plate 104a,b.

The plates 104a,b and threaded bolts 116 can be made of stainless steel, titanium, and/or other biologically acceptable material such as polyetheretherketone (PEEK). In one embodiment, the grips 214a,b can similarly be comprised of a biologically acceptable material such as stainless steel, titanium, and/or other material such as PEEK, with the surface that comes into contact with the spinous process having a roughened or uneven surface. The contacting surface can, for example, be knurled or it can contain spikes to allow the grips 214a,b to engage the bone of the spinous processes. In other embodiments, the grips 214a,b can be comprised of silicon or other biologically acceptable polymer or material (such as presented below with respect to the spacers). The material can be somewhat deformable and can conform to the surface of the spinous processes.

As shown in FIGS. 1 and 2A, the system 100 has a single clamp positioned at each of two spinous processes, each clamp being comprised of two grips 214a,b on opposite sides of an associated spinous process. However, in other embodiments, a plurality of clamps (with associated grips 214a,b) can be positioned at selected spinous processes. Thus, for each surface of each spinous process there can be two or more grips. With several grips, each grip can be tightened against a portion of the surface of a spinous process independently of the other adjacent grip that is tightened against a different portion of the same surface of the spinous process. This system can accordingly accommodate uneven surfaces of the spinous processes with each grip tightened against a portion of a surface of a spinous process that is not even with another portion of the surface of the spinous process.

Referring again to FIG. 1, the plates 104a,b are secured together with pins 110. A pin 110 can have a threaded bore for receiving a screw or bolt having a hexagonal, slotted, or other type of head at each end of the pin 110. Alternatively, one or both ends of the pin 110 can be threaded for receiving a nut, or lug for example, or other fastener. The pin 110 can be made of a material similar to the plates 104a,b, for example, the pin 110 can be made of stainless steel, titanium or other biologically acceptable material. At least one fastener for each pin 110 is tightened so that the pins pull the plates 104a,b toward one another as desired. Alternatively, the pins 110 can have a main body diameter thicker than the height of a slot 106 with a thinner threaded end for passing through the slot, thereby predefining a space between plates 104a,b.

The clamps are adjusted as desired either before or after the fastener(s) of the pins 110 are tightened, thereby allowing the clamps to grip the spinous processes, making the system 100 rigid. A spacer 102 is moveably and rotatably connected with each pin 110 between plates 104a,b. The spacer 102 is substantially cylindrical in shape with an elliptical cross-section sized to conform to a gap between spinous processes in which the spacer 102 is to be inserted. The elliptical spacer 102 has opposite, slightly curved (or relatively flat) surfaces that can distribute the load placed on the spacer by the spinous processes between which the spacer 102 is positioned. The spacer 102 further has curved ends connecting the slightly curved surfaces. The curved ends point substantially posteriorly and anteriorly. The anteriorly pointing ends approach the spine. In other embodiments the spacer 102 can have an egg-shaped cross-section with the curved end pointing toward the spine being smaller that the curved end pointing posteriorly in order to allow the spacer 102 to more closely approach the spine. In still other embodiments, the spacer 102 can have a cross-section having an ovoid, oval or even spherical shape, for example. One of ordinary skill in the art can appreciate the different cross-sectional shapes with which the spacer 102 can be formed in order to distribute load within the spacer 102.

One advantage of using the spacer 102 depicted in FIG. 1 is that the spacer 102 can be partially rotated and repositioned with respect to the system 100 in order to optimize positioning of the spacer 102 between spinous processes. The system 100 is thus designed to account for the various spine structures found in patients. Without having to remove bone from the spine or make multiple adjustments to a hardware system, the spacers 102 and also the grips 214a,b allow the system 100 to easily conform to the structure of an associated spine. Further, ease of use and placement allow procedures for implanting the system 100 to be carried out more quickly and with less potential trauma to the surgical site. Still further, as indicated above, the spacers 102 can be located closer to the spine where the bone is stronger, thus affording maximum load bearing and stabilizing support relative to the spine. Such load bearing and stabilizing support is advantageous when the system 100 is used as an adjunct to the fusion of adjacent vertebral bodies. It is to be understood that the cortical bone or the outer bone of the spinous processes is stronger at an anterior position adjacent to the vertebral bodies of the vertebra than at a posterior position distally located from the vertebral bodies.

Still further, for load bearing it is advantageous for the spacer 102 to be close to the vertebral bodies. In order to facilitate this and to accommodate the anatomical form of the bone structures, the spacer 102 rotates relative to the system 100 as the spacer 102 is inserted between the spinous processes and/or urged toward the vertebral bodies so that the spacer 102 is optimally positioned between the spinous processes and the system 100 is optimally positioned relative to the spinous processes. The shape of the spacer 102 is designed so that it conforms to the area that the spacer 102 is inserted into. However, one of ordinary skill in the art will appreciate that the spacer 102 is not limited to having an elliptical cross-section. For example, the spacer 102 can be substantially spherical in cross-section or egg shaped as set forth above.

As can be seen in FIG. 1, the spacers 102 can be of various sizes. Thus for example, using imaging prior to surgery, the anatomy of the individual patient can be determined and the system 100 assembled to suit the particular patient. Additionally, during surgery the physician can be provided with a kit having different sized spacers 102 and the physician can assemble the system 100 with appropriately sized spacers 102 to fit the anatomy of the patient. In this embodiment the pins 110 can be comprised of rods with threaded bores at each end that receive bolts or screws used to secure the pins between two plates 104a,b with the spacer 102 rotatably mounted on the pins 110.

Figure 3:
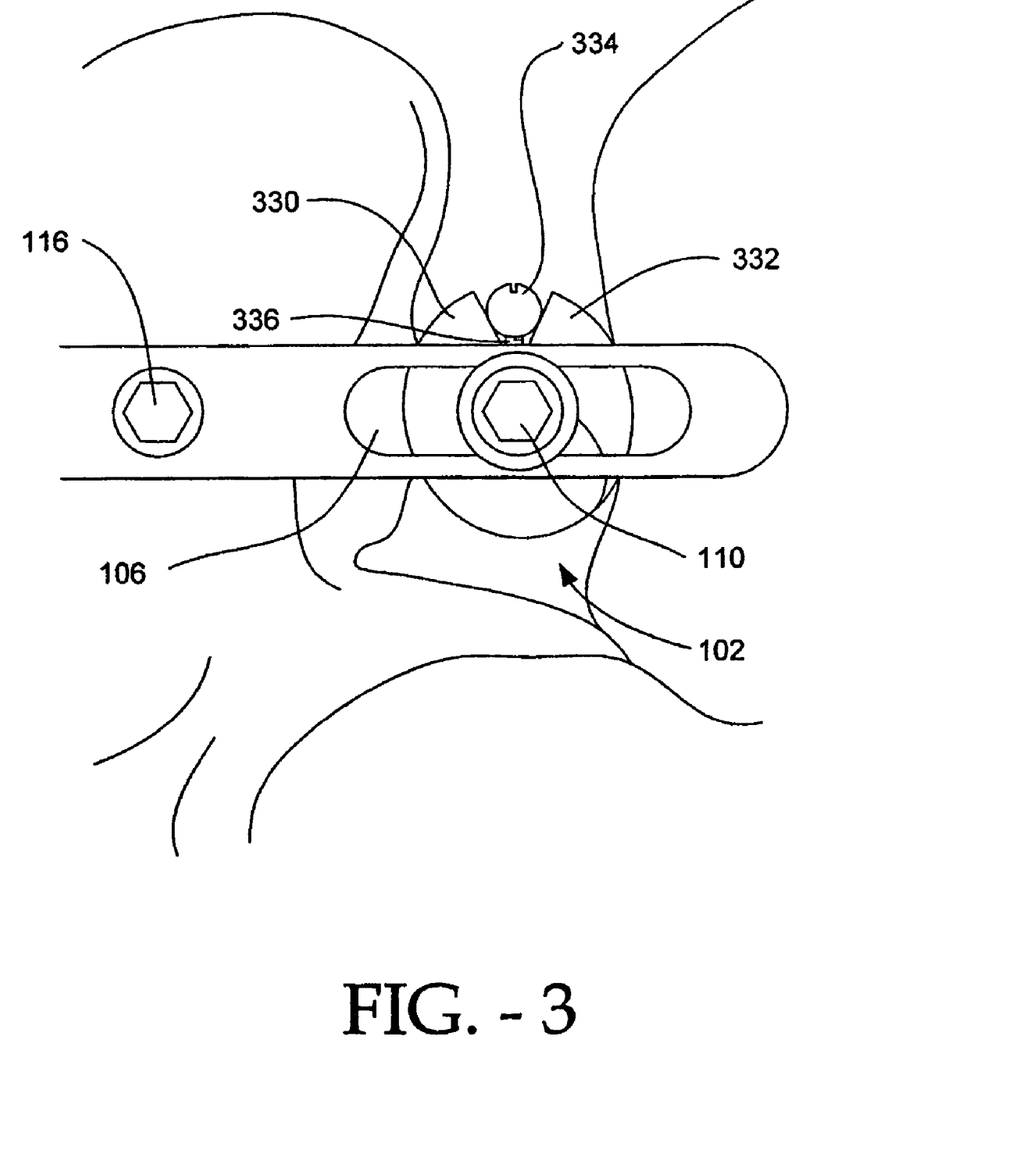
FIG. 3 is a side view of an alternative embodiment of the invention with an expanding spacer.

In other embodiments, the spacer 102 can be comprised of two portions adjustably connected by a hinge to allow expansion of the spacer 102. For example, as shown in FIG. 3, the spacer 102 is comprised of a first portion 330 and a second portion 332 that together have a minor dimension that can be adjusted by rotating a ball 334 connected with a lead screw 336, such that the ball 334 alternatively forces the minor dimension to expand or allows the minor dimension to collapse. Such a spacer is described in pending U.S. Patent Application No. 60/421,921, entitled "INTERSPINOUS PROCESS APPARATUS AND METHOD WITH A SELECTABLY EXPANDABLE SPACER" by James F. Zucherman, Ken Y. Hsu, and Charles J. Winslow, incorporated herein by reference.

The spacer 102 can be made of a polymer, such as a thermoplastic, and can be formed by extrusion, injection, compression molding and/or machining techniques. Specifically, the spacer 102 can be made of a polyketone such as PEEK. One type of PEEK is PEEK 450G, which is an unfilled PEEK approved for medical implantation available from Victrex of Lancashire, Great Britain. Other sources of this material include Gharda located in Panoli, India. PEEK 450G has appropriate physical and mechanical properties and is suitable for carrying and spreading the physical load between the spinous process. For example in this embodiment the PEEK has the following approximate properties:

1 Density 1.3 g/cc Rockwell M 99 Rockwell R 126 Tensile Strength 97 MPa Modulus of Elasticity 3.5 GPa Flexural Modulus 4.1 Gpa It should be noted that the material selected may also be filled. For example, other grades of PEEK available and contemplated include 30% glass-filled or 30% carbon-filled PEEK, provided such materials are cleared for use in implantable devices by the FDA or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

As can be appreciated, other suitable biologically acceptable thermoplastic or thermoplastic polycondensate materials that resist fatigue, have good memory, are flexible and/or deflectable, have very low moisture absorption and have good wear and/or abrasion resistance, can be used without departing from the scope of the invention other materials that can be used include polyetherketoneketone (PEKK), polyetherketone (PEK), polyetherketoneetherketoneketone (PEKEKK), and polyetheretherketoneketone (PEEKK), and generally a polyaryletheretherketone. Further, other polyketones can be used, as well as other thermoplastics. Still further, silicon can also be used or the spacer can be made of titanium and/or stainless steel.

Reference to appropriate polymers that can be used in the spacer can be made to the following documents, all of which are incorporated herein by reference: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials. Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

As mentioned above, each spacer 102 can be connected with a pin 110 that adjustably connects the first plate 104a with the second plate 104b. In one embodiment, each plate 104a,b has three slots 106 spaced and sized such that the slots 106 span approximately the width of the gap between the associated adjacent spinous processes when a patient is standing up. The length of the slots 106 should allow for necessary adjustment of the spacers 102 so that the anatomy of the adjacent spinous processes can be accommodated with the spinous processes immobilized between the spacers 102. In the system 100 shown in FIG. 1, the middle of three slots 106 is sized larger than the slots 106 on either end of the plates. However, in other embodiments, the slots 106 can be sized relative to one another based on the vertebral bodies that are intended to be immobilized.

Figure 4A:
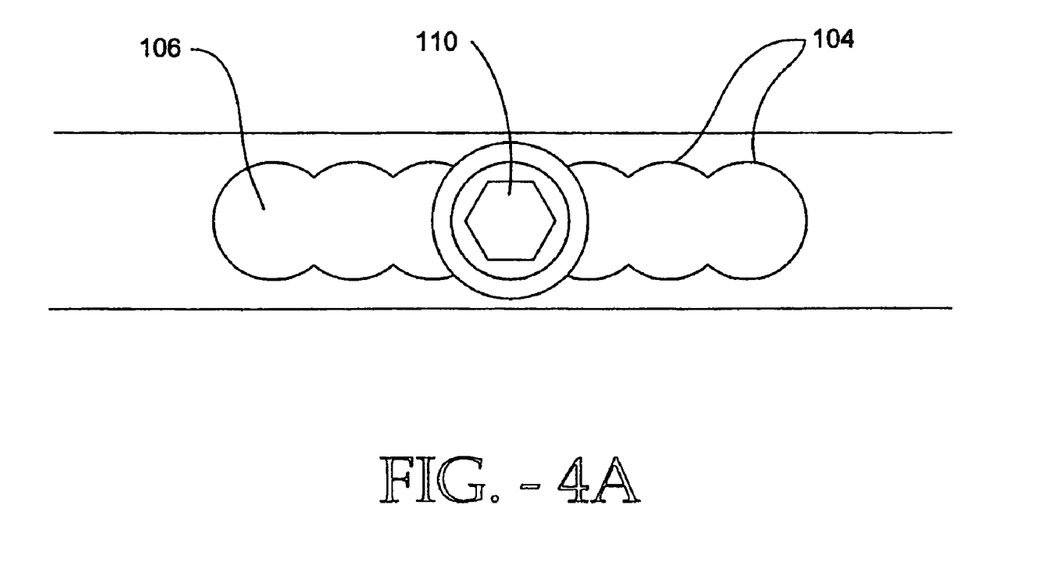
FIG. 4A is a side view of an alternative embodiment of the invention with a slot for positioning a pin having lobed cut-outs.
Figure 4B:
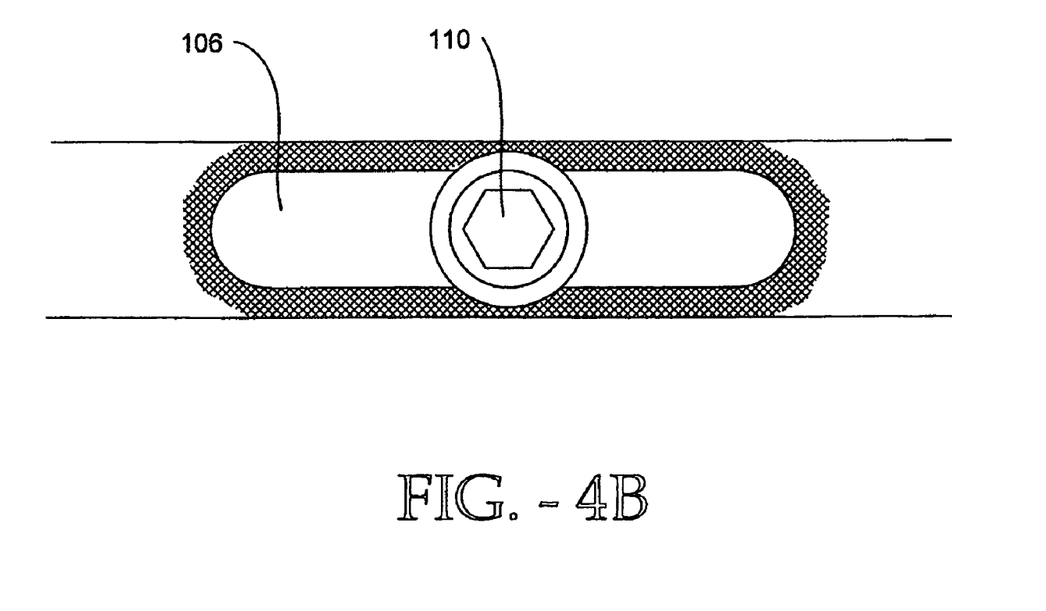
FIG. 4B is a side view of an alternative embodiment of the invention with a slot for positioning a pin having a knurled periphery.

As described above, a pin 110 can be fitted into a slot 106 in each plate 104a,b. The width of the slot 106 allows the pin 110 to be optimally positioned within the gap between spinous processes, while still being fixable to the plates 104a, b. The pin 110 can be fixedly connected with each plate 104a,b by a bolt, screw, nut or other fastener, optionally coupled with a washer. To prevent the plates 104a,b and pins 110 from slipping and shifting relative to one another, a number of different type of slots can be employed to fix the pin 110 in position. As shown in FIG. 4A, one type of slot 106 that can be used is a slot having cut-outs, lobes, or scallops 440 sized such that the cut-outs, lobes or scallops 440 have diameters slightly larger than the diameter of the pin 110, but are separated such that the adjacent cut-outs, lobes, or scallops are joined at a space narrower than the diameter of the pin 110 so that the pin 110 is prevented from sliding to the adjacent position. Another type of slot 106, shown in FIG. 4B, includes knurls around each slot's periphery, intended to be used with a knurled washer placed between a fastener and a plate 104a,b. The knurls on the respective surfaces grip each other when the fastener is tightened, preventing the pin 110 from moving in the slot 106. One of ordinary skill in the art can appreciate the different means for fixing a pin 110 in a slot 106 to prevent the pin 110 from moving relative to the plate 104a,b.

Figure 5:
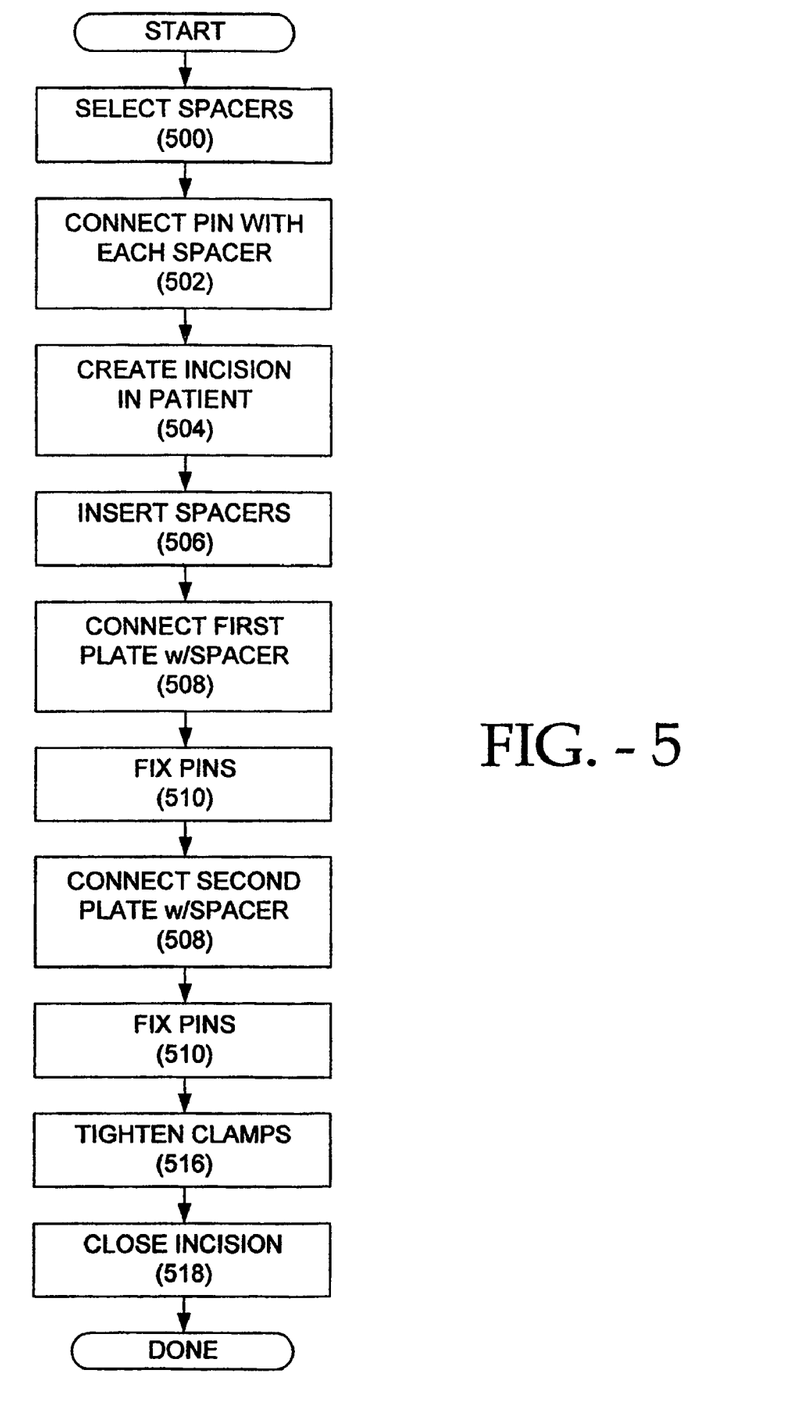
FIG. 5 is a representation of a method for immobilizing adjacent spinous processes in accordance with one embodiment of the present invention.

In alternative embodiments, the system 100 can comprise one or two plates 104a,b with spacers 102 rotatably secured thereto (foregoing the use of grips). The system 100 can be implanted and the position of the spacers 102 can be adjusted relative to the slots 106, the one or two plates 104a,b, and the spinous processes in order to immobilize the spinous processes FIG. 5 is a block diagram showing steps for performing a method for inserting a system 100 into a patient in order to immobilize vertebral bodies in accordance with the present invention. As shown in first block 500, a first, second and third spacer 102 is selected according to the size of the gap between spinous processes that each spacer 102 will occupy. Each spacer 102 is moveably connected with an associated pin 110 (step 502). An incision is made in the patient proximate to vertebral bodies to be immobilized (step 504), and the spinous processes and surrounding tissues are exposed. Each spacer 102 is then inserted into position between targeted spinous processes (step 506) and allowed to rotate and adjust to conform as closely as possible to the contours of the space. A first plate 104a is inserted into the patient and positioned such that a first end of each pin 110 fits into a slot 106 (step 508). Each pin 110 is fixedly connected to the first plate 104a by a fastener, for example a bolt or slotted screw (step 510). A second plate 104b is inserted into the patient and positioned such that a second end of each pin 110 fits into a slot 106 (step 512). Each pin 110 is fixedly connected to the second plate 104b by a fastener, for example a bolt or slotted screw (step 514). Finally, the grips 214a,b are incrementally tightened so that each clamp grips an associated spinous process (step 516). The incision is closed (step 518).

In other embodiments, a method in accordance with the present invention can be applied where there are more or less than three spacers 102, and/or more or less than two clamps. The configuration of a system 100 will depend on the area intended to be immobilized, and the requirements of the patient.

Other methods of insertion, include having the system 100 fully assembled prior to insertion. For this method, the surgical site is prepared and then the system 100 is pushed down over the ends of the spinous processes until the system 100 rests in a desired location. At this point the grips 214a,b are tightened in place about the spinous processes.

Still alternatively, the system 100 can be partially assembled with the spacers 102 assembled with a first plate 104a. This subassembly is positioned alongside of the spinous processes and the spacers 102 are urged between the adjacent spinous processes. When the spacers 102 are positioned, the second plate 104b is secured to the system 100.

The foregoing description of preferred embodiments of the present invention has been provided for the purposes of illustration and description. It is not intended to be exhaustive or to limit the invention to the precise forms disclosed. Many modifications and variations will be apparent to one of ordinary skill in the relevant arts. The embodiments were chosen and described in order to best explain the principles of the invention and its practical application, thereby enabling others skilled in the art to understand the invention for various embodiments and with various modifications that are suited to the particular use contemplated. Other features, aspects, and objects of the invention can be obtained from a review of the specification, the figures, and the claims. It is intended that the scope of the invention be defined by the claims and their equivalence.

What is claimed is:

1. A system for immobilizing adjacent spinous processes, comprising:
   a first plate;
   a second plate connected with the first plate;
   a first grip associated with the first plate and coupled to the first plate so as to be transversely moveable relative to both the first and second plates;
   a second grip associated with the second plate and coupled to the second plate so as to be transversely moveable relative to both the first and second plates;
   a spacer rotatably connected between the plates, the spacer adapted to be positioned between adjacent spinous processes;
   wherein the first grip and the second grip are adapted to frictionally contact opposite sides of one of the adjacent spinous process;
   wherein the spacer is rotatable in order to adjust the orientation of the spacer relative to the spinous processes.

2. The system for immobilizing adjacent spinous processes of claim 1, wherein the first grip and the second grip are adapted to be adjusted relative to the spinous process such that the first and the second grip are movable towards and away from the spinous process.

3. The system for immobilizing adjacent spinous processes of claim 2, wherein the first grip and the second grip include one of a bolt and a slotted screw for adjusting the first grip and the second grip.

4. The system for immobilizing adjacent spinous processes of claim 1, wherein the spacer can be expanded.

5. The system for immobilizing adjacent spinous processes of claim 1, wherein the spacer is substantially elliptical in cross-section.

6. The system for immobilizing adjacent spinous processes of claim 1, wherein the spacer is adapted to be positioned close to a spine and adjacent to portions of the spinous processes to spread the load placed upon the spacer by the adjacent spinous processes.

7. The system for immobilizing adjacent spinous processes of claim 1, wherein the spacer is movably attached to the system so that the spacer can attach at two or more locations on the system.

8. The system for immobilizing adjacent spinous processes of claim 1, wherein the spacer rotates about an axis extending laterally between the adjacent spinous processes when the first grip and the second grip frictionally contact the opposite sides.

9. The system for immobilizing adjacent spinous processes of claim 8, further comprising a pin, wherein the first plate includes a slot for positioning a first end of the pin and the second plate includes a slot for positioning a second end of the pin such that the position of the pin is adjustable relative to the first plate and the second plate.

10. The system for immobilizing adjacent spinous processes of claim 9, wherein the slot includes a plurality of lobes for positioning the pin such that the pin does not slip within the slot.

11. The system for immobilizing adjacent spinous processes of claim 9, further comprising knurls surrounding the slot for preventing the pin from slipping within the slot.

12. A system for immobilizing adjacent spinous processes, comprising:
- a first plate;
- a second plate connected with the first plate by at least one pin; and
- at least one clamp adapted to grip a spinous process, the at least one clamp including:
  - a first grip connected with the first plate, the first grip adapted to be positioned in contact with a first side of the spinous process; and
  - a second grip connected with the second plate, the second grip adapted to be positioned in contact with a second side of the spinous process;
- wherein the at least one clamp is adapted to frictionally contact the adjacent spinous process; and
- a spacer rotatably mounted between the first and second plates on the at least one pin, the spacer adapted to be positioned between spinous processes.

13. The system for immobilizing adjacent spinous processes of claim 12, wherein a position of the at least one pin can be adjusted along a portion of the length of the first and second plates.

14. The system for immobilizing adjacent spinous processes of claim 13, wherein the portion of the length of the first and second plates is defined by a length of at least one slot.

15. The system for immobilizing adjacent spinous processes of claim 14, wherein the at least one slot includes a plurality of one of cut-outs, lobes, and scallops such that the pin can be positioned to prevent the pin from slipping within the at least one slot.

16. The system for immobilizing adjacent spinous processes of claim 14, including knurls associated with at least one slot to prevent the pin from slipping within the at least one slot.

17. The system for immobilizing adjacent spinous processes of claim 12, wherein the at least one spacer is substantially elliptical in cross-section.

18. The system for immobilizing adjacent spinous processes of claim 12, wherein the at least one spacer is adapted to be positioned close to a spine and adjacent to portions of the spinous processes to spread the load placed upon the at least one spacer by the adjacent spinous processes.

19. The system for immobilizing adjacent spinous processes of claim 17, wherein the at least one spacer is movably attached to the system so that the at least one spacer can attach at two or more locations on the system.

20. The system of claim 12 wherein:
- said a first grip is moveably connected with the first plate so as to be moveable generally transverse to both the first and second plates, and
- said a second grip is moveably connected with the second plate so as to be moveable generally transverse to both the first and second plates.

* * * * *